(12) United States Patent
Park (10) Patent No.: US 11,904,038 B2
(45) Date of Patent: Feb. 20, 2024

(54) COMPOSITION FOR PREVENTING HAIR LOSS OR PROMOTING HAIR DEVELOPMENT, COMPRISING PHELLANDRENE AS ACTIVE INGREDIENT

(71) Applicant: INDUSTRY-ACADEMIC COOPERATION FOUNDATION, YONSEI UNIVERSITY, Seoul (KR)

(72) Inventor: Tae Sun Park, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 664 days.

(21) Appl. No.: 16/759,135

(22) PCT Filed: Oct. 25, 2018

(86) PCT No.: PCT/KR2018/012680
§ 371 (c)(1),
(2) Date: Jul. 6, 2020

(87) PCT Pub. No.: WO2019/083287
PCT Pub. Date: May 2, 2019

(65) Prior Publication Data
US 2020/0337961 A1 Oct. 29, 2020

(30) Foreign Application Priority Data
Oct. 26, 2017 (KR) .................. 10-2017-0140343

(51) Int. Cl.
| | | |
|---|---|---|
| *A61K 8/31* | (2006.01) | |
| *A61K 9/00* | (2006.01) | |
| *A61K 31/015* | (2006.01) | |
| *A61Q 5/02* | (2006.01) | |
| *A61Q 5/12* | (2006.01) | |
| *A61Q 19/00* | (2006.01) | |

(52) U.S. Cl.
CPC .............. *A61K 8/31* (2013.01); *A61K 9/0014* (2013.01); *A61K 9/0056* (2013.01); *A61K 9/0095* (2013.01); *A61K 31/015* (2013.01); *A61Q 5/02* (2013.01); *A61Q 5/12* (2013.01); *A61Q 19/007* (2013.01)

(58) Field of Classification Search
CPC ...... A61K 8/31; A61K 9/0014; A61K 9/0056; A61K 9/0095; A61K 31/015; A61K 9/06; A61K 9/08; A61K 9/145; A61K 9/2018; A61K 9/4858; A61K 45/06; A61K 47/26; A61P 17/14; A61Q 7/00; A23L 33/10; A23V 2002/00; A23V 2200/318
See application file for complete search history.

(56) References Cited

FOREIGN PATENT DOCUMENTS

| | | |
|---|---|---|
| DE | 4401274 A1 | 7/1995 |
| KR | 10-0757237 B1 | 9/2007 |
| KR | 2011-0060660 A | 6/2011 |
| WO | 2011/051945 A1 | 5/2011 |

OTHER PUBLICATIONS

Behzadi et al., DE 44 01 274 A1—Jul. 20, 1995—English machine translation, 11 pages (Year: 1995).*
Lee et al., "Effects of Lavender Oil on Hair Growth-Relevant Enzyme Activity and Cytokine Expression in C57BL/6 Mice" Journal of Investigative Cosmetology vol. 12, No. 1, pp. 1-8 (2016) (Year: 2016).*
B. H. Lee et al., "Hair Growth-Promoting Effects of Lavender Oil in C57BL/6 Mice", Toxicological Research, 2016, pp. 103-108, vol. 32, No. 2.
International Search Report for PCT/KR2018/012680 dated May 17, 2019 [PCT/ISA/210].
Written Opinion for PCT/KR2018/012680 dated May 17, 2019 [PCT/ISA/237].

* cited by examiner

*Primary Examiner* — Aradhana Sasan
(74) *Attorney, Agent, or Firm* — Sughrue Mion, PLLC (57) ABSTRACT

Provided is a composition for preventing hair loss or promoting hair development, comprising, as an active ingredient, phellandrene or a pharmaceutically acceptable salt thereof. More specifically, provided is a pharmaceutical composition, a quasi-drug composition, a cosmetic composition, or a health functional food composition, for preventing hair loss, treating hair loss, promoting hair development, or promoting hair growth, the composition comprising phellandrene or a salt thereof as an active ingredient. The composition not only contains, as an active ingredient, a natural compound having no adverse effects even when administered for a long period of time with respect to hair loss, a chronic disease, but also exhibits excellent and stable efficacy in hair development and hair growth, which allows the composition to be usefully used as an agent for preventing or treating hair loss, or a pharmaceutical, quasi-drug, cosmetic, or health functional food composition for promoting hair development or hair growth.

5 Claims, 5 Drawing Sheets
Specification includes a Sequence Listing.

FIG. 6

SEQUENCE LISTING

<160> NUMBER OF SEQ ID NOS: 8

<210> SEQ ID NO 1
<211> LENGTH: 23
<212> TYPE: DNA
<213> ORGANISM: Artificial
<220> FEATURE:
<223> OTHER INFORMATION: LEF_F primer

<400> SEQUENCE: 1
tgccaaatat gaataacgac cca    23

```
<210> SEQ ID NO 2
<211> LENGTH: 21
<212> TYPE: DNA
<213> ORGANISM: Artificial
<220> FEATURE:
<223> OTHER INFORMATION: LEF_R primer

<400> SEQUENCE: 2
gagaaaagtg ctcgtcactg t                                              21

<210> SEQ ID NO 3
<211> LENGTH: 22
<212> TYPE: DNA
<213> ORGANISM: Artificial
<220> FEATURE:
<223> OTHER INFORMATION: Cyclin D_F primer

<400> SEQUENCE: 3
atgttcgtgg cctctaagat ga                                             22

<210> SEQ ID NO 4
<211> LENGTH: 22
<212> TYPE: DNA
<213> ORGANISM: Artificial
<220> FEATURE:
<223> OTHER INFORMATION: Cyclin D_R primer

<400> SEQUENCE: 4
caggttccac ttgagcttgt tc                                             22

<210> SEQ ID NO 5
<211> LENGTH: 20
<212> TYPE: DNA
<213> ORGANISM: Artificial
<220> FEATURE:
<223> OTHER INFORMATION: VEGF_F primer

<400> SEQUENCE: 5
ttcatggatg tctatcagcg                                                20

<210> SEQ ID NO 6
<211> LENGTH: 20
<212> TYPE: DNA
<213> ORGANISM: Artificial
<220> FEATURE:
<223> OTHER INFORMATION: VEGF_R primer

<400> SEQUENCE: 6
catctctcct atgtgctggc                                                20

<210> SEQ ID NO 7
<211> LENGTH: 23
<212> TYPE: DNA
<213> ORGANISM: Artificial
<220> FEATURE:
<223> OTHER INFORMATION: IGF-1_F primer

<400> SEQUENCE: 7
cttcagttcg tgtgtggaga cag                                            23

<210> SEQ ID NO 8
<211> LENGTH: 16
<212> TYPE: DNA
<213> ORGANISM: Artificial
<220> FEATURE:
<223> OTHER INFORMATION: IGF-1_R primer
```

```
<400> SEQUENCE: 8
cgccctccga ctgctg                                                    16
```

COMPOSITION FOR PREVENTING HAIR LOSS OR PROMOTING HAIR DEVELOPMENT, COMPRISING PHELLANDRENE AS ACTIVE INGREDIENT

CROSS REFERENCE TO RELATED APPLICATIONS

This application is a National Stage Application No. PCT/KR2018/012680, filed on Oct. 25, 2018, which claims priority from Korean Patent Application No. KR10-2017-0140343 filed Oct. 26, 2017, the disclosure of which is incorporated herein in its entirety by reference.

TECHNICAL FIELD

The present application claims priority to Korean Patent Application No. 10-2017-0140343, filed on Oct. 26, 2017, which is incorporated herein by reference in its entirety.

The present invention relates to a composition for preventing hair loss or promoting hair development, comprising, as an active ingredient, phellandrene or a pharmaceutically acceptable salt thereof. More specifically, the present invention relates to a pharmaceutical composition, a quasi-drug composition, a cosmetic composition, or a health functional food composition, for preventing hair loss, treating hair loss, promoting hair development, or promoting hair growth, the composition comprising, as an active ingredient, phellandrene or a salt thereof.

BACKGROUND ART

According to the health insurance medical expense payment data from 2001 to 2008, analyzed by the National Health Insurance Policy Research Institute of the Korean National Health Insurance Service, the actual number of patients who had received medical treatment for "hair loss condition" was estimated at 103,000 people in 2001, at 142,000 people in 2005, and at 165,000 people in 2008. The number had increased by 60% over the last 7 years. In terms of age, the actual number of patients in their 20's to 40's was estimated at 114,000 people which account for 69.5% of the total patients; and the number of patients in their 10's or younger was estimated at 22,000 or higher people. In terms of sex, as of 2008, the actual number of patients was estimated at 84,000 for males and 80,000 for females, indicating that males are slightly more than females. In terms of types of "hair loss" condition, as of 2008, the actual number of patients under the Korean Health Insurance was estimated at 130,000 people for alopecia areata, at 20,000 people for cicatricial alopecia, at 9,000 people for androgenetic alopecia, and at 8,000 people for other nonscarring hair loss.

Meanwhile, according to the data from the international meeting for research and discussion on hair and cosmetic surgery held in June 2003, it was found that about 250 million people worldwide were patients with hair loss, and the incidence of hair loss was about 30% to 65% in people aged 24 to 50. In China, as of 2008, the population of hair loss reached about 300 million. About 30% of the male population in their 30's and about 50% of the male population in their 50's showed signs of hair loss. The number of patients with hair loss increases every year by about 10% to 15%. In Japan, according to the data from a survey conducted by a company that sells wigs and provides hair transplant surgery service, as of 2007, the incidence of hair loss was 26.5% in Japanese people, and the estimated number of patients with hair loss was expected to be about 12.93 million.

Currently, agents for treating hair loss are largely classified into drug products, quasi-drug products, and cosmetic products. As a specialized pharmaceutical product that can be purchased only with a doctor's prescription, "Propecia", developed and sold by Merck in the United States, is mentioned. Finasteride, the main ingredient of Propecia, was approved for hair loss treatment by the US FDA in December 1997. Finasteride is a drug for inhibiting 5-α-reductase that converts testosterone to dihydrotestosterone (DHT), and serves to grow soft hair into thick and long hair. Although this is effective in ameliorating hair loss in the short term, adverse effects such as erectile dysfunction, decreased sexual function, and male breast enlargement are accompanied.

Minoxidil is mentioned as an over-the-counter drug that can be purchased without a doctor's prescription as its safety and effectiveness are recognized. Minoxidil was approved as the first external-use drug for treating hair loss by the US FDA in December, 1997. This drug has an effect of improving blood circulation and opening potassium channels so that hair growth is promoted. However, such a drug may be accompanied by local reactions such as itching and rash, and may cause tachycardia to occur.

As quasi-drug products that have been approved by the Korea Food and Drug Administration for their function of hair loss prevention and hair growth and can be sold in supermarkets and convenience stores under the notification of the Minister of Health and Welfare in Korea, "Moballyeok Competent" manufactured by CJ Lion, "Hair Tonic" manufactured by Moracle, and "MO & MORE" manufactured by LG Household & Health Care Ltd. are representatively mentioned. As toiletries, shampoos or products used for the scalp or hair which maintain or enhance the health of skin and hair are being marketed.

The human hair cycle is largely classified into growth phase (anagen), regression phase (catagen), and resting phase (telogen). The growth phase is a period during which hair grows fast due to active hair dermal papilla's activity and vigorous cell division. The duration of the growing phase varies depending on the type of hair; and in a case of hair on the head, its growing phase lasts approximately 3 to 6 years. Hair at its growth phase accounts for 80% to 90% of the entire hair. Those who are undergoing hair loss tend to have a hair cycle with a shorter growth phase and a longer resting phase, so that among the entire hair, a proportion of hair at its growing phase decreases. The regression phase is a period during which the growth phase of hair ends and hair production gradually slows down so that cell division and growth eventually stop. The regression phase lasts approximately 1 to 1.5 months, and approximately 1% of the entire hair is at this phase. The resting phase, which is the last stage of growth, is a period during which the hair follicle and the hair dermal papilla are completely separated from each other, and thus the hair follicle shrinks and the hair root goes further upwards, so that the hair falls out. The resting phase lasts 3 to 4 months, and 4% to 14% of the entire hair is at this phase. When the resting phase ends and the hair dermal papilla's activity becomes active again, a hair dermal papilla of new hair is made, during which the hair at its resting phase is pushed out and completely falls out of the scalp.

To date, Wnt/β-catenin signal pathway is a well-known signaling system involved in hair follicle development and hair growth. When the Wnt ligand binds to its receptor, beta-catenin in the cytoplasm is stabilized so that its degradation does not occur and its migration to the cell nucleus increases, thereby regulating expression of a target gene. According to the findings of the research time of Walter Birchmeier listed in the International Journal of Cell in 2001, it was identified that hair loss appears in experimental animals in which beta-catenin has been knocked-down, indicating that beta-catenin plays an important role in preventing hair loss and promoting hair growth. In particular, it is well known that activation of protein kinase A (PKA), AKT, glycogen synthase-3β (GSK-3β), and the like causes the Wnt/beta-catenin signal pathway to be activated (Monick, 2001, Akira 2005). PKA, a representative cAMP-dependent enzyme, is activated by cAMP to inhibit degradation of beta-catenin in the cytoplasm so that stabilization thereof is increased, promote migration thereof to the cell nucleus, and regulate expression of a target gene (Akira, 2005).

Meanwhile, phellandrene is an essential oil component of various plants, and is mainly contained in plants such as dill (*Anethum graveolens* L.), *Echinophora cinerea*, and pepper tree (*Schinus molle*). Phellandrene is known to be an edible safe substance. Phellandrene has been approved for use as flavor and fragrance agents by the Flavor and Extract Manufacturers' Association (FEMA), the Food and Drug Administration (FDA), the Korea Food and Drug Administration (KFDA), the Council of Europe (COE), and the Joint FAO/WHO Expert Committee on Food Additives (JECFA), and has been used industrially for the purpose of producing flavor and fragrance.

In addition, phellandrene has been used as a flavor and fragrance agent to produce geranium, rose, or tea flavor in the manufacture of perfumes, produce fresh, mint, pepper, spice, or wood flavor, or the like in food, and add sweetness to citrus flavor. However, it is not known that phellandrene has an effect of preventing hair loss or promoting hair development.

Technical Problem

Accordingly, the present inventors tried to find a naturally-derived compound capable of preventing hair loss or promoting hair development or hair growth without causing adverse effects. As a result, the present inventors have identified that phellandrene effectively promotes hair development and hair growth and prevents hair loss, thereby completing the present invention.

Therefore, the present invention has been devised to solve the above-mentioned problems, and an object thereof is to provide a pharmaceutical composition for preventing or treating hair loss, or promoting hair development or hair growth, comprising, as an active ingredient, phellandrene or a pharmaceutically acceptable salt thereof.

Another object of the present invention is to provide a quasi-drug composition for preventing or ameliorating hair loss, or promoting hair development or hair growth, comprising, as an active ingredient, phellandrene or a pharmaceutically acceptable salt thereof.

Yet another object of the present invention is to provide a cosmetic composition for preventing or ameliorating hair loss, or promoting hair development or hair growth, comprising, as an active ingredient, phellandrene or a cosmetically acceptable salt thereof.

Still yet another object of the present invention is to provide a health functional food composition for preventing or ameliorating hair loss, or promoting hair development or hair growth, comprising, as an active ingredient, phellandrene or a sitologically acceptable salt thereof.

However, the technical problem to be achieved by the present invention is not limited to the above-mentioned problems, and other problems not mentioned will be clearly understood by those skilled in the art from the following description.

Solution to Problem

Accordingly, the present invention provides a pharmaceutical composition for preventing or treating hair loss, or promoting hair development or hair growth, comprising, as an active ingredient, phellandrene or a pharmaceutically acceptable salt thereof.

According to a preferred embodiment of the present invention, the composition is capable of increasing expression of at least one selected from the group consisting of (β-catenin, protein kinase A Cα (PKA Cα), lymphoid enhancer factor-1 (LEF-1), insulin-like growth factor-1 (IGF-1), vascular endothelial growth factor (VEGF), and cyclin D.

According to another preferred embodiment of the present invention, the pharmaceutical composition may be a formulation for skin external use selected from the group consisting of a cream, a gel, a patch, a spray, an ointment, a plaster, a lotion, a liniment, a paste, and a cataplasm.

In addition, the present invention provides a quasi-drug composition for preventing or ameliorating hair loss, or promoting hair development or hair growth, comprising, as an active ingredient, phellandrene or a pharmaceutically acceptable salt thereof.

In addition, the present invention provides a cosmetic composition for preventing or ameliorating hair loss, or promoting hair development or hair growth, comprising, as an active ingredient, phellandrene or a cosmetically acceptable salt thereof.

According to yet another preferred embodiment of the present invention, the cosmetic composition may be a formulation which is a scalp tonic, a scalp lotion, a scalp cream, a scalp serum, a scalp essence, a scalp ampoule, a scalp treatment, a scalp conditioner, a scalp shampoo, a scalp pack, a hair tonic, a hair lotion, a hair cream, a hair spray, a hair mousse, a hair gel, a hair conditioner, a hair shampoo, a hair rinse, a hair pack, a hair treatment, an eyebrow growth solution, an eyelash growth solution, an eyelash enhancer, a shampoo for pets, or a conditioner for pets.

In addition, the present invention provides a health functional food composition for preventing hair loss or promoting hair development, comprising, as an active ingredient, phellandrene or a sitologically acceptable salt thereof.

In addition, the present invention provides a method for preventing or treating hair loss, or promoting hair development or hair growth, comprising a step of administering, to an individual, a composition that comprises, as an active ingredient, phellandrene or a pharmaceutically acceptable salt thereof, or a step of causing the individual to take the composition.

In addition, the present invention provides a use of a composition that comprises, as an active ingredient, phellandrene or a pharmaceutically acceptable salt thereof, for preventing or treating hair loss, or promoting hair development or hair growth.

Advantageous Effects of Invention

The present invention has been devised to solve the above-mentioned problems and is intended to provide a composition for preventing or ameliorating hair loss, or promoting hair development or hair growth, comprising, as an active ingredient, phellandrene or a pharmaceutically acceptable salt thereof.

The composition of the present invention not only contains, as an active ingredient, a natural compound having no adverse effects even when administered for a long period of time with respect to hair loss, a chronic disease, but also exhibits excellent and stable efficacy in hair development and hair growth, which allows the composition to be usefully used as an agent for preventing or treating hair loss, or a quasi-drug, cosmetic, or health functional food composition for promoting hair development or hair growth.

DETAILED DESCRIPTION OF INVENTION

Hereinafter, the present invention will be described in detail.

As described above, in addition to hair loss caused by changes in hormone secretion, hair loss caused by stress is increasing, which has led to increased demands for a pharmaceutical composition or the like capable of preventing hair loss and/or promoting hair development. However, among naturally-derived compounds known to be safe to the human body, few reports have been made about compounds capable of effectively preventing hair loss and/or promoting hair development.

The phellandrene of the present invention can significantly exhibit a hair development promotion effect in hair-removed mice or the like by regulating expression of hair development-related genes and proteins in the skin tissue.

Thus, the phellandrene has an effect of providing a composition effective in preventing hair loss and promoting hair growth.

Accordingly, the present invention provides a pharmaceutical composition for preventing or treating hair loss, or promoting hair development or hair growth, the composition comprising, as an active ingredient, phellandrene or a pharmaceutically acceptable salt thereof.

As used herein, the term "phellandrene" refers to a monoterpene-based compound having a structural formula of $C_{10}H_{16}$ and a molecular weight of 136 g/mol. Phellandrene having two isomers in total is divided, depending on its structure, into alpha-phellandrene (α-phellandrene) represented by Formula 1 and beta-phellandrene (β-phellandrene) represented by Formula 2. Alpha-phellandrene has the IUPAC name of 2-methyl-5-(1-methylethyl)-1,3-cyclohexadiene and is also called menthadiene, p-menta-1,5-diene, α-fellandrene, or dihydro-p-cymene. Beta-phellandrene has the IUPAC name of 3-methylene-6-(1-methylethyl)cyclohexene and is also called 2-p-menthadiene or p-mentha-1(7),2-diene. Phellandrene is a colorless liquid, and is insoluble in water and very soluble in alcohol and propylene glycol.

Phellandrene is an essential oil component of various plants and is known as an edible safe substance. Phellandrene has been used industrially for the purpose of producing flavor and fragrance. According to oral toxicity test results, it was reported that the half lethal dose ($LD_{50}$ value) of phellandrene is 5,700 mg/kg in rats. On the other hand, according to percutaneous toxicity test results for rabbits, the $LD_{50}$ value was found to be 5,000 mg/kg. In addition, as a result of clinical trials, it has been reported that there is no skin irritation or sensitization reaction (sensitivity) in 4% solution.

On the other hand, it has been reported that the known physiological functions of phellandrene are to induce apoptosis in leukemia cells (Lin et al. Alpha-phellandrene-induced DNA damage and affect DNA repair protein expression in WEHI-3 murine leukemia cells in vitro. *Environmental Toxicology* 30: 1322-1330, 2015) and to serve as an anti-inflammatory agent through regulation of neutrophil migration and mast cell stabilization (Siqueira et al. α-Phellandrene, a cyclic monoterpene, attenuates inflammatory response through neutrophil migration inhibition and mast cell degranulation. *Life Sciences* 160: 27-33, 2016).

Accordingly, oral administration of phellandrene at 0.1 mg/kg to 1,500 mg/kg, preferably 10 mg/kg to 1,000 mg/kg, has very little or no toxicity, which allows phellandrene to be used as a cosmetic composition, a health functional food composition, a drug composition, or a quasi-drug composition.

In the present invention, the phellandrene may include phellandrene hydrates, phellandrene derivatives, and the like within a range having the same efficacy, and may include solvates or stereoisomers thereof.

The present invention has revealed a mechanism by which the phellandrene regulates expression of hair development-related genes and proteins in the skin tissue, thereby identifying a novel use of phellandrene for preventing hair loss or promoting hair development.

As used herein, the term "hair loss" refers to a phenomenon in which hair completely comes out of the scalp. A person who is undergoing hair loss has a hair growth cycle with a shorter growth phase and a longer resting phase. As demonstrated in the following examples, phellandrene converts hair from a resting phase to a growth phase and increases expression of hair development- and hair development-related growth factors in the skin tissue. From this viewpoint, it can be identified that phellandrene has an effect of preventing, ameliorating, or treating hair loss.

As used herein, the term "hair development" refers to generation of hair on the scalp, and the term "hair growth" refers to an increase in hair length (that is, growth of hair) and is used interchangeably with another term "hair development" used in in the art.

The composition of the present invention may increase expression of at least one selected from the group consisting of β-catenin, protein kinase A Cα (PKA Cα), lymphoid enhancer factor-1 (LEF-1), insulin-like growth factor-1 (IGF-1), vascular endothelial growth factor (VEGF), and cyclin D. Specifically, as shown in Example 2 of the present invention, it was identified that the composition of the present invention increases expression of (3-catenin gene related to the Wnt/β-catenin signaling system involved in entry of the hair follicle cycle into a growth phase in the skin tissue; and it was identifiable that the composition of the present invention significantly increases expression of all of lymphoid enhancer factor-1 (LEF-1), insulin-like growth factor-1 (IGF-1), vascular endothelial growth factor (VEGF), and cyclin D which are hair development promotion-related genes. In addition, it was identifiable that the composition of the present invention significantly increases expression levels of the proteins or genes as compared with a group treated with Minoxidil, which is currently a representative drug that can promote hair development and hair growth. Therefore, the composition of the present invention is less harmful to the human body than conventional synthetic compositions, and can be usefully used as a composition for hair development or hair development which shows various and stable hair development and hair development promotion efficacy.

The phellandrene is preferably used as a composition for skin external use. A pharmaceutical composition for skin external use which comprises, as an active ingredient, the phellandrene of the present invention may be prepared and used as a pharmaceutical composition in the form of a preparation for skin external use for preventing hair loss and ameliorating or promoting hair development which includes, but is not limited to, a cream, a gel, a patch, a spray, an ointment, a plaster, a lotion, a liniment, a paste, and a cataplasm.

The phellandrene of the present invention may be used in the form of a pharmaceutically acceptable salt. As the salt, an acid addition salt formed with a pharmaceutically acceptable free acid is useful. The acid addition salt is obtained from inorganic acids such as hydrochloric acid, nitric acid, phosphoric acid, sulfuric acid, hydrobromic acid, hydroiodic acid, nitrous acid, or phosphorous acid, and non-toxic organic acids such as aliphatic mono- and dicarboxylates, phenyl-substituted alkanoates, hydroxyalkanoates and alkanedioates, aromatic acids, aliphatic and aromatic sulfonic acids. These pharmaceutically non-toxic salts include sulfates, pyrosulfates, bisulfates, sulfites, bisulfites, nitrates, phosphates, monohydrogen phosphates, dihydrogen phosphates, metaphosphates, pyrophosphates, chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butyne-1,4-dioates, hexane-1,6-dioates, benzoates, chlorobenzoates, methylbenzoates, dinitrobenzoates, hydroxybenzoates, methoxybenzoates, phthalates, terephthalates, benzenesulfonates, toluenesulfonates, chlorobenzenesulfonates, xylenesulfonates, phenylacetates, phenylpropionates, phenylbutyrates, citrates, lactates, β-hydroxybutyrates, glycolates, malates, tartrates, methanesulfonates, propanesulfonates, naphthalene-1-sulfonates, naphthalene-2-sulfonates, and mandelates.

The acid addition salt according to the present invention may be prepared by a conventional method, for example, by dissolving the phellandrene in an excess of aqueous acid solution, and precipitating the salt using a water-miscible organic solvent such as methanol, ethanol, acetone, or acetonitrile. The acid addition salt according to the present invention may be prepared by heating the equal amounts of phellandrene and acid or alcohol in water or alcohol, and then evaporating the mixture to dryness or subjecting the precipitated salt to suction filtration.

In addition, a pharmaceutically acceptable metal salt may be prepared using a base. The alkali metal or alkaline earth metal salt is obtained, for example, by dissolving the compound in an excess of alkali metal hydroxide or alkaline earth metal hydroxide solution, filtering an undissolved compound salt, and evaporating the filtrate to dryness. Here, as the metal salt, it is pharmaceutically suitable to prepare a sodium, potassium, or calcium salt. In addition, a silver salt corresponding thereto is obtained by reacting an alkali or alkaline earth metal salt with a suitable silver salt (for example, silver nitrate).

In addition, the phellandrene of the present invention includes not only pharmaceutically acceptable salts, but also all salts, hydrates, and solvates that can be prepared by conventional methods.

The addition salt according to the present invention may be prepared by a conventional method, for example, by dissolving phellandrene in a water-miscible organic solvent such as acetone, methanol, ethanol, or acetonitrile, adding thereto an excess of aqueous organic acid or inorganic acid solution, and then performing precipitation or crystallization. Subsequently, the addition salt may be obtained by evaporating the solvent or excess acid in this mixture and then performing drying, or may be prepared by subjecting the precipitated salt to suction filtration.

In a case where the composition of the present invention is used as a drug product, a pharmaceutical composition comprising, as an active ingredient, phellandrene or a pharmaceutically acceptable salt thereof may be prepared into various oral or parenteral dosage forms as shown below and administered, upon clinical administration. However, the present invention is not limited thereto.

Examples of formulations for oral administration include tablets, pills, hard/soft capsules, liquids, suspensions, emulsifiers, syrups, granules, elixirs, and the like. These formulations contain, in addition to an active ingredient, a diluent (for example, lactose, dextrose, sucrose, mannitol, sorbitol, cellulose, and/or glycine), a lubricant (for example, silica, talc, stearic acid and a magnesium or calcium salt thereof, and/or polyethylene glycol). Tablets may also contain a binder such as magnesium aluminum silicate, starch paste, gelatin, methylcellulose, sodium carboxymethylcellulose, and/or polyvinylpyrrolidine, and in some cases, may contain a disintegrant such as starch, agar, alginic acid or a sodium salt thereof, or a boiling mixture, and/or an absorbent, a colorant, a flavoring agent, and a sweetener.

The pharmaceutical composition comprising, as an active ingredient, the phellandrene of the present invention or a pharmaceutically acceptable salt thereof may be parenterally administered, and the parenteral administration is carried out by subcutaneous injection, intravenous injection, intramuscular injection, or intrathoracic injection. Here, in order to prepare a formulation for parenteral administration, the phellandrene or a pharmaceutically acceptable salt thereof is mixed with a stabilizer or buffer in water, to prepare a solution or suspension, and the solution or suspension may be prepared as an ampoule or vial unit dosage form. The composition may be sterilized, and/or contain adjuvants such as a preservative, a stabilizer, a hydration agent or emulsifier, a salt for regulating osmosis, and/or a buffer, and other therapeutically useful substances. The composition may be made into a preparation by a conventional method such as mixing, granulation, or coating.

In addition, a dosage of the compound of the present invention to the human body may vary depending on the patient's age, body weight, and sex, the dosage form, the health condition, and the severity of a disease. The dosage is, in general, 0.001 to 1,000 mg/day and preferably 0.01 to 500 mg/day, based on an adult patient having a body weight of 60 kg; and the dosage may be administered once a day or several times a day in divided doses at regular time intervals according to the determination of a doctor or pharmacist.

In addition, the present invention provides a quasi-drug composition for preventing or ameliorating hair loss, or promoting hair development or hair growth, comprising, as an active ingredient, phellandrene or a pharmaceutically acceptable salt thereof. The details of the phellandrene are as described above.

In a case where the phellandrene of the present invention is used as an active ingredient of the quasi-drug composition, the phellandrene that exhibits an effect of preventing hair loss and promoting hair growth may be added as it is or may be used with other quasi-drugs or ingredients of the quasi-drugs, in which the phellandrene may be appropriately used according to a conventional method. A mixing ratio of active ingredients may be suitably determined depending on the intended use.

The quasi-drug composition for preventing hair loss and promoting hair growth of the present invention is not particularly limited in terms of its formulation, and may be variously formulated in the form of quasi-drugs known in the art to exhibit an effect of preventing hair loss and promoting hair growth. The formulated quasi-drugs include a scalp tonic, a scalp lotion, a scalp cream, a scalp serum, a scalp essence, a scalp ampoule, a scalp treatment, a scalp conditioner, a scalp shampoo, a scalp pack, a hair tonic, a hair lotion, a hair cream, a hair spray, a hair mousse, a hair gel, a hair conditioner, a hair shampoo, a hair conditioning rinse, a hair pack, a hair treatment, an eyebrow growth solution, an eyelash growth solution, an eyelash enhancer, a shampoo for pets, a conditioner for pets, a hand sanitizer, a detergent soap, a soap, an antiseptic cleanser, a wet tissue, a mask, an ointment, a patch, a filter filler, or the like, with all quasi-drugs in the usual sense being included therein.

In addition, for each formulation, the quasi-drug composition for preventing hair loss and promoting hair growth may be blended with other ingredients that may be selected in a predetermined manner depending on other factors including the formulation of the quasi-drug, the intended use thereof, or the like. A mixing ratio of active ingredients may be suitably determined depending on the intended use. The composition may contain, for example, conventional adjuvants such as a thickening agent, a stabilizer, a solubilizer, a vitamin, a pigment, and a fragrance, carriers, and the like.

A content of each of the ingredients is preferably 0.0001% to 10% by weight based on the total weight. In a case where the content is greater than 10% by weight, there is a disadvantage that color and stability are deteriorated at the time of preparing the composition; and in a case where the content is less than 0.0001% by weight, there is a disadvantage in that a marginal effect is exhibited. The quasi-drug composition comprising, as an active ingredient, the phellandrene of the present invention may be usefully used as a material for quasi-drug products because it has little toxicity and adverse effects on cells as identified from the therapeutic index thereof.

In addition, the present invention provides a cosmetic composition for preventing or ameliorating hair loss, or promoting hair development or hair growth, the composition comprising, as an active ingredient, phellandrene or a pharmaceutically acceptable salt thereof.

Ingredients contained in the cosmetic composition of the present invention include, in addition to phellandrene or a pharmaceutically acceptable salt thereof as an active ingredient, ingredients commonly used in cosmetic compositions, for example, conventional adjuvants such as an antioxidant, a stabilizer, a solubilizer, a vitamin, a pigment, and a fragrance, and carriers.

The cosmetic composition of the present invention may be prepared in any formulation conventionally used in the art. For example, the cosmetic composition may be formulated as a solution, a suspension, an emulsion, a paste, a gel, a cream, a lotion, a powder, a soap, a surfactant-containing cleanser, oil, a powder foundation, an emulsion foundation, a wax foundation, a spray, or the like; however, the present invention is not limited thereto.

In a case where the formulation of the present invention is a paste, a cream, or a gel, animal oil, vegetable oil, wax, paraffin, starch, tragacanth, a cellulose derivative, polyethylene glycol, silicone, bentonite, silica, talc, zinc oxide, or the like may be used as a carrier component.

In a case where the formulation of the present invention is a powder or a spray, lactose, talc, silica, aluminum hydroxide, calcium silicate, or polyamide powder may be used as a carrier component. In particular, in the case where the formulation is a spray, it may further contain a propellant such as chlorofluorohydrocarbon, propane/butane, or dimethyl ether.

In a case where the formulation of the present invention is a solution or an emulsion, a solvent, a solubilizing agent, or an emulsifying agent is used as a carrier component, and examples thereof include water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan.

In a case where the formulation of the present invention is a suspension, a liquid diluent such as water, ethanol, or propylene glycol, a suspending agent such as ethoxylated isostearyl alcohol, polyoxyethylene sorbitol ester, or polyoxyethylene sorbitan ester, microcrystalline cellulose, aluminum metahydroxide, bentonite, agar, tragacanth, or the like may be used as a carrier component.

In a case where the formulation of the present invention is a surfactant-containing cleanser, aliphatic alcohol sulfate, aliphatic alcohol ether sulfate, sulfosuccinic acid monoester, isethionate, an imidazolinium derivative, methyltaurate, sarcosinate, fatty acid amide ether sulfate, alklyamidobetaine, aliphatic alcohol, fatty acid glyceride, fatty acid diethanolamide, vegetable oil, a lanolin derivative, ethoxylated glycerol fatty acid ester, or the like may be used as a carrier component.

In addition, the present invention provides a health functional food composition for preventing or ameliorating hair loss, or promoting hair development or hair growth, comprising, as an active ingredient, phellandrene or a pharmaceutically acceptable salt thereof.

The food composition according to the present invention may be prepared in various forms according to conventional methods known in the art. The food composition may be prepared by adding the phellandrene of the present invention to any one of common foods including, but not limited to, beverages (including alcoholic beverages), fruits and processed foods thereof (for example, canned fruit, bottled fruit, jam, marmalade, and the like), fish, meat, and processed foods thereof (for example, ham, sausage, corned beef, and the like), bread and noodles (for example, udon, soba, ramen, spaghetti, macaroni, and the like), fruit juice, various types of drinks, cookies, taffies, dairy products (for example, butter, cheese, and the like), edible vegetable oil and fat, margarine, vegetable proteins, retort foods, frozen foods, various seasonings (for example, soy bean paste, soy sauce, other sauces, and the like), and the like. In addition, a nutritional supplement may be prepared by adding the phellandrene of the present invention to a capsule, tablet, pill, or the like; however, the present invention is not limited thereto. In addition, as a health functional food, the phellandrene itself of the present invention, which has been liquefied, granulated, encapsulated, or pulverized, may be prepared in the form of tea, juice, or drink, and consumed (as a health beverage); however, the present invention is not limited thereto. In addition, in order to be used in the form of a food supplement, the phellandrene of the present invention may be prepared in the form of a powder or concentrate and used. In addition, the phellandrene of the present invention may be prepared in the form of a composition by being mixed with other active ingredients known to have an effect of preventing hair loss and promoting hair development.

In a case where the phellandrene of the present invention is used for a health beverage, the health beverage composition may contain, as additional ingredients, various flavoring agents, natural carbohydrates, or the like as in ordinary beverages. The above-mentioned natural carbohydrates may include monosaccharides such as glucose and fructose; disaccharides such as maltose and sucrose; polysaccharides such as dextrin and cyclodextrin; and sugar alcohol such as xylitol, sorbitol, and erythritol. As the sweetening agent, a natural sweetening agent such as thaumatin and a *stevia* extract; a synthetic sweetening agent such as saccharin and aspartame, or the like may be used. A proportion of the natural carbohydrate may be about 0.01 to 0.04 g and preferably about 0.02 to 0.03 g, per 100 mL of the composition of the present invention.

In addition, the phellandrene of the present invention may be contained as an active ingredient in a health functional food for preventing hair loss and promoting hair development; and in such a case, the phellandrene is used in an amount effective to achieve an effect of preventing hair loss and promoting hair growth. The amount of the phellandrene is not particularly limited and is preferably 0.01% to 100% by weight with respect to the total weight of the entire composition. The food composition of the present invention may be prepared by mixing of phellandrene together with other active ingredients known to have an effect of preventing hair loss and promoting hair growth.

In addition to the above-mentioned ingredients, the health food of the present invention may further contain various nutrients, vitamins, electrolytes, savoring agents, coloring agents, pectic acid, salts of pectic acid, alginic acid, salts of alginic acid, organic acids, protective colloids, a thickening agent, a pH adjusting agent, a stabilizer, a preservative, glycerin, alcohol, a carbonating agent, or the like. In addition, the health food of the present invention may further contain fruit flesh for preparing a natural fruit juice, a fruit juice beverage, or a vegetable beverage. These ingredients may be used independently or in admixture. A proportion of such additives is not very critical and is generally selected in a range of 0.01 to 0.1 parts by weight per 100 parts by weight of the composition of the present invention.

Hereinafter, the present invention will be described in detail by way of examples. However, these examples are intended to describe the present invention in more detail, and the scope of the present invention is not limited to these examples.

EXAMPLES

Example 1. Evaluation of Phellandrene on Promoting Hair Development 1-1. Experiment Method 1) Sample Preparation and Culture of Human Hair Dermal Papilla Cells The phellandrene used in this experiment was purchased from Sigma Aldrich Co., Ltd.

Human hair dermal papilla cells were purchased from PromoCell GmbH (Heidelberg, Germany). The human hair dermal papilla cells were cultured in an incubator at 37° C., 5% $CO_2$ using HFDPC medium (PromoCell, Germany) with fetal bovine serum (FBS) and Dulbecco's modified Eagle's medium (DMEM; Gibco BRL, Gaithersburg, MD, USA). Due to the nature of the cells, cells at passages 2 to 5 were used for all experiments.

2) MTT Assay Analysis

The human hair dermal papilla cells were dispensed into 24-well plates to $1\times10^5$ cells/well, and then cultured for 24 hours in an incubator at 37° C., 5% $CO_2$ so that the cells are stabilized. Treatment with samples at respective concentrations (0, 10, 20, 50, 100, 200, 400 μg/ml) was performed and culture was performed for 24 hours. Then, treatment with 100 ul of 3-(4,5-dimethylthiazol-2-yl)-2,5-diphenyltetrazolium bromide (MTT; Sigma Aldrich, St. Louis, USA) reagent at a concentration of 200 mg/ml was performed and culture was performed again for 4 hours. After removing the medium, the precipitate (formazan) was dissolved in DMSO and the absorbance was measured at a wavelength of 540 nm. A proliferation rate thereof was evaluated based on the absorbance of a control group containing only DMSO.

1-2. Experiment Results

Figure 1:
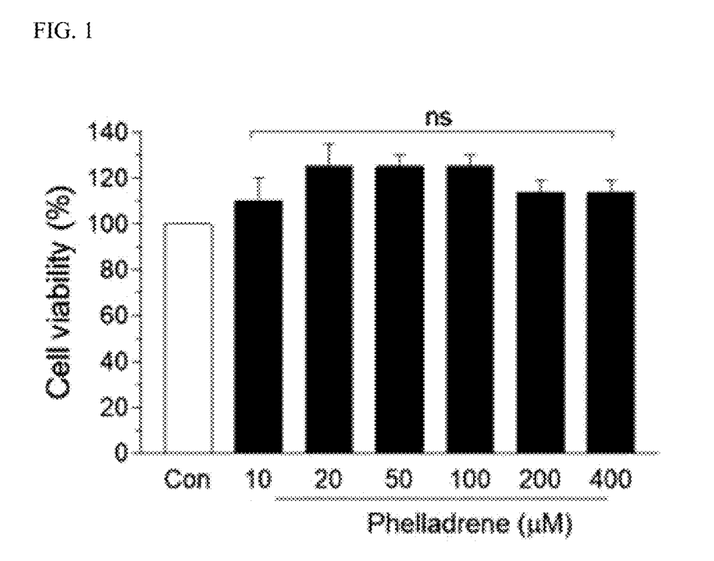
FIG. 1 illustrates a graph showing results obtained by evaluating toxicity of phellandrene in human hair dermal papilla cells. Each value is expressed as mean±standard error (SEM). ns=p>0.05, *=p<0.05, =p<0.01, *=p<0.001 [one-way ANOVA, Tukey's test]

1) Presence or Absence of Toxicity of Phellandrene in Human Hair Dermal Papilla Cells The group containing only DMSO was set as a control group. Treatment with phellandrene at respective concentrations was performed. Then, culture was performed for 24 hours, and cell viability was measured through an MTT assay. As a result, phellandrene did not affect the cell viability up to a concentration of 400 μg/ml (FIG. 1).

Figure 2:
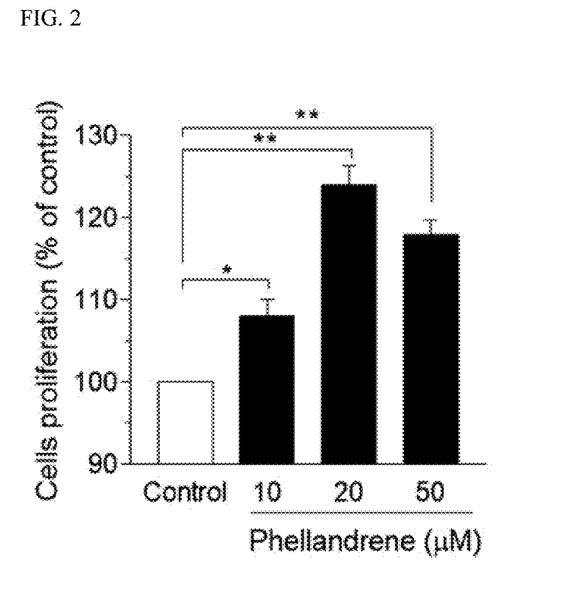
FIG. 2 illustrates a graph showing results obtained by evaluating cell proliferation efficacy of phellandrene in human hair dermal papilla cells. Each value is expressed as mean±standard error (SEM). ns=p>0.05, *=p<0.05, =p<0.01, *=p<0.001 [one-way ANOVA, Tukey's test]

2) Cell Proliferation Efficacy of Phellandrene in Human Hair Dermal Papilla Cells It was identified that in a case where the human hair dermal papilla cells are treated with phellandrene at concentrations of 10, 20, and 50 μM, respectively, their proliferation rate increases significantly by 10.8%, 24%, and 18%, respectively (FIG. 2). Thereafter, experiments were conducted by setting the optimal effective concentration of phellandrene to 20 μM.

Example 2: Identification of Mechanism for Hair Development Promotion, Caused by Phellandrene, in Human Hair Dermal Papilla Cells 2-1. Experiment Method 1) Enzyme-Linked Immunosorbent Assay (ELISA)

The human hair dermal papilla cells were dispensed into 12-well plates to $3 \times 10^4$ cells/well, and then the culture solutions were treated with phellandrene at 20 μM. DMSO was used as a negative control group. The phellandrene-treated culture solutions were collected after 24 hours, and experiments were conducted using human VEGF ELISA Kit (Enzo Life Sciences, NY, USA), human IGF-1 ELISA kit (Enzo Life Sciences, NY, USA), and cAMP complete ELISA kit (Enzo Life Sciences, NY, USA), respectively, according to the manufacturers' protocol.

2) Protein Extraction and Western Blot Analysis

The supernatant of human hair dermal papilla cells, obtained by performing treatment with phellandrene at 20 μM and performing culture, was homogenized with a lysis buffer, and then centrifuged at 13,000×g for 20 minutes at 4° C. Protein quantification was performed by Bradford assay. 40 μg of the protein was electrophoresed on 10% SDS polyacrylamide gel and then transferred to nitrocellulose membranes. The protein was allowed to react with each of PKA Cα, β-catenin, β-actin, and GAPDH antibody (Cell Signaling Technology, Danvers, MA, USA). Each protein's signal was visualized with a chemiluminescent detection system (Amersham), and then the band's thickness was quantified using the Quantity One Analysis Software (Bio-Rad Laboratories).

3) RNA Isolation Method Using Trizol Method

In the present invention, in order to identify activity of phellandrene on human hair dermal papilla cells (DPCs), when the DPCs reached 70% to 80% confluency, treatment with phellandrene at 20 μM was performed, and then culture was performed under a condition of 5% $CO_2$ and 37° C. 24 hours after the treatment, the cells were collected and total RNA was extracted with Trizol Reagent (Gibco BRL, USA). The total RNA was quantified by absorbance measurement at 260 nm.

4) Real Time-Polymerase Chain Reaction (RT-PCR) Analysis

After isolation of RNA, cDNA was synthesized by performing reverse transcription using oligo dT primers and SuperScript reverse transcriptase (GIBCOBRL, Gaithersburg, MD, USA). PCR was performed using, as a template, cDNA obtained through reverse transcription and using, as primers, 5' and 3' flanking sequences of the gene's cDNA to be amplified. Here, required primers were obtained by making a request for synthesis with a company specializing in primer manufacturing (BIONEER CORPORATION, Korea) and used. The primer sequences are shown in Table 1. To a mixture obtained by mixing of 5 μl of 10× reaction buffer [100 mM KCL, 20 mM Tris-HCl (pH 8.0), 2.5 mM $MgCl_2$], 4 μl of 10 mM dNTP, and 1 μl each of 0.2 μM sense and antisense primers, were added 2 μl of the completed cDNA reaction mixture and 2.5 unit of Taq polymerase (Takara, Japan). Then, the volume was adjusted with 50 μl of distilled water, and PCR was performed using a PCR instrument. PCR conditions were set to 94° C. for 4 minutes, 94° C. (30 seconds), 30 cycles of [52° C. (30 seconds), 72° C. (45 seconds)], and 72° C. for 10 minutes.

TABLE 1

Primer sequences used in RT-PCR

| Gene description | Primers | Sequences (5'→3') | Length (bp) |
|---|---|---|---|
| Lymphoid enhancer factor (LEF) | F | TGCCAAATATGAATAACGACCCA (SEQ ID NO: 1) | 150 |
| | R | GAGAAAAGTGCTCGTCACTGT (SEQ ID NO: 2) | |
| Cyclin D | F | ATGTTCGTGGCCTCTAAGATGA (SEQ ID NO: 3) | 138 |
| | R | CAGGTTCCACTTGAGCTTGTTC (SEQ ID NO: 4) | |
| Vascular endothelial growth factor (VEGF) | F | TTCATGGATGTCTATCAGCG (SEQ ID NO: 5) | 234 |
| | R | CATCTCTCCTATGTGCTGGC (SEQ ID NO: 6) | |
| Insulin growth factor-1 (IGF-1) | F | CTTCAGTTCGTGTGTGGAGACAG (SEQ ID NO: 7) | 75 |
| | R | CGCCCTCCGACTGCTG (SEQ ID NO: 8) | |

2-2. Experiment Results

Figure 3:
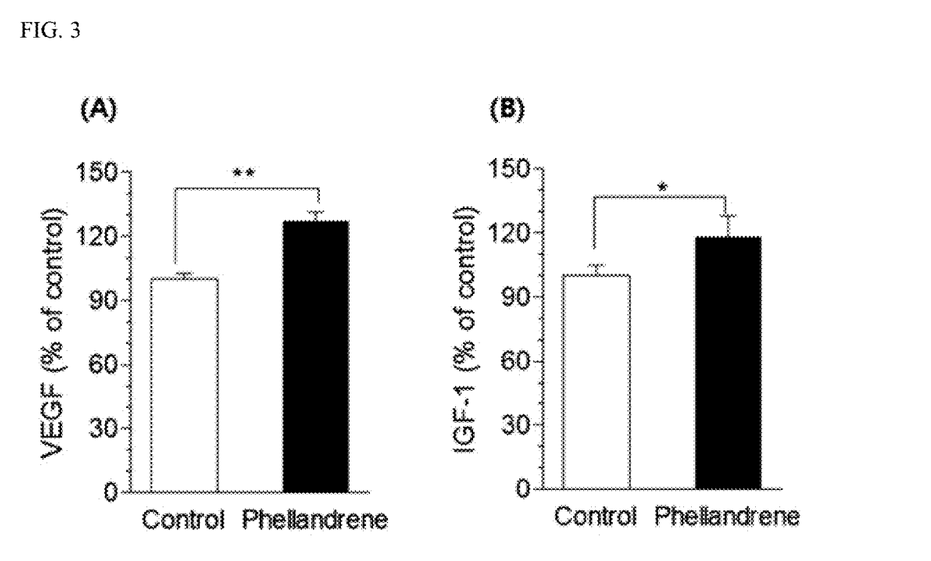
FIG. 3 illustrates a graph showing an effect of phellandrene on increase in the concentration of hair development promotion growth factors (VEGF and IGF-1) in human hair dermal papilla cells. Each value is expressed as mean±standard error (SEM). ns=p>0.05, *=p<0.05, =p<0.01, *=p<0.001 [one-way ANOVA, Tukey's test]

1) Effect of Phellandrene on Increase in Concentration of Hair Development Promotion Growth Factors (VEGF and IGF-1) in Human Hair Dermal Papilla Cells In human hair dermal papilla cells, phellandrene significantly increased the concentrations of VEGF and IGF-1, which are growth factors involved in hair development promotion, by 27% ((A) of FIG. 3) and 18% ((B) of FIG. 3), respectively. Therefore, it can be seen that the phellandrene according to the present invention has excellent hair development promotion efficacy.

Figure 4:
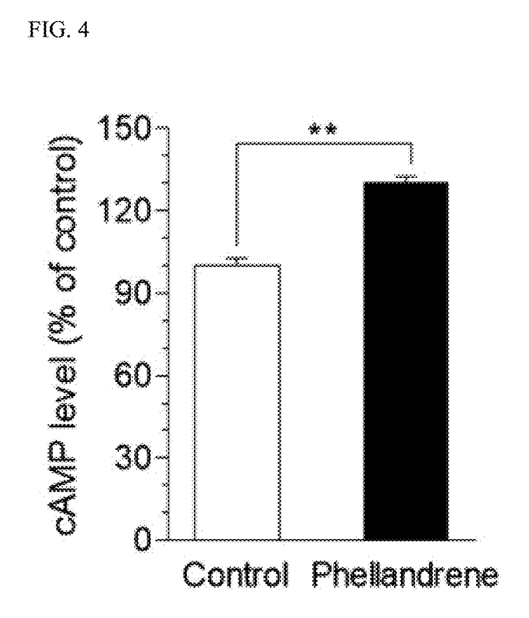
FIG. 4 illustrates a graph showing an effect of phellandrene on increase in the concentration of cAMP in human hair dermal papilla cells. Each value is expressed as mean±standard error (SEM). ns=p>0.05, *=p<0.05, =p<0.01, *=p<0.001 [one-way ANOVA, Tukey's test]

2) Effect of Phellandrene on Increase in Concentration of cAMP of in Human Hair Dermal Papilla Cells cAMP is a mediator that amplifies signals from hormones or growth factors bound to receptors on the cell surface and transmits the signals into cells. cAMP, which is synthesized in the cytoplasm, is known to regulate activity of PKA Cα. In human hair dermal papilla cells, phellandrene significantly increased the cAMP concentration by 30% (FIG. 4). This indicates that phellandrene increases the cAMP concentration in human hair dermal papilla cells, and thus activates the Wnt/β-catenin hair development regulation signaling system that is induced by PKA Cα.

Figure 5:
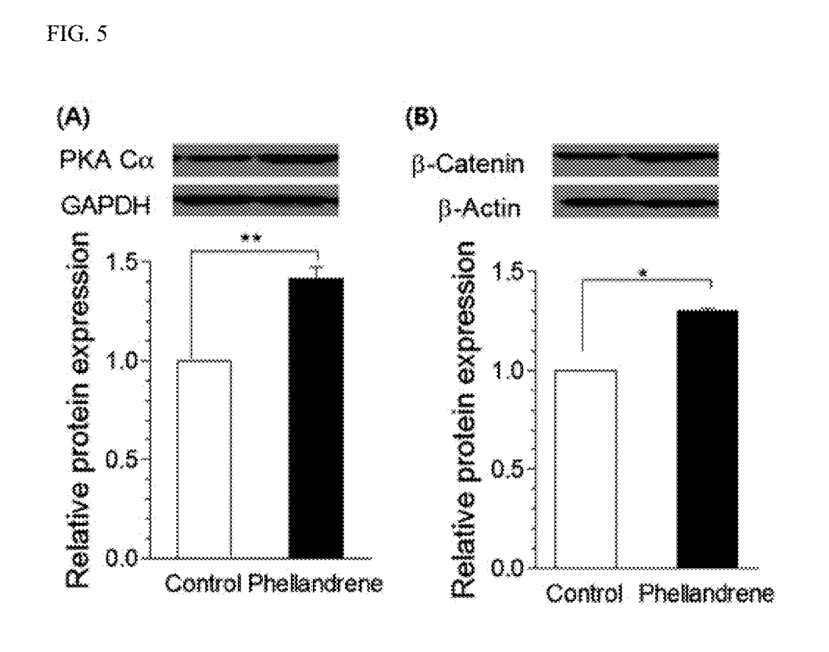
FIG. 5 illustrates a graph showing an effect of phellandrene on increase in expression of hair development regulation signaling proteins (PKA Cα, β-catenin) in human hair dermal papilla cells. Each value is expressed as mean±standard error (SEM). ns=p>0.05, *=p<0.05, =p<0.01, *=p<0.001 [one-way ANOVA, Tukey's test]

3) Effect of Phellandrene on Increase in Expression of Hair Development Regulation Signaling Proteins (PKA Cα,β-Catenin) in Human Hair Dermal Papilla Cells PKA Cα inhibits degradation of β-catenin in the cytoplasm and promotes migration thereof to the cell nucleus, and β-catenin is known as a signaling protein that regulates expression of target genes that promote hair growth in the cell nucleus. In human hair dermal papilla cells, phellandrene significantly increased expression of PKA Cα by 42% ((A) of FIG. 5) and significantly increased, in the cell nucleus, expression of β-catenin by 30% ((B) of FIG. 5). From these results, it can be seen that phellandrene increases expression of hair development regulation signaling proteins, thereby inducing proliferation of human hair dermal papilla cells and promoting hair growth.

Figure 6:
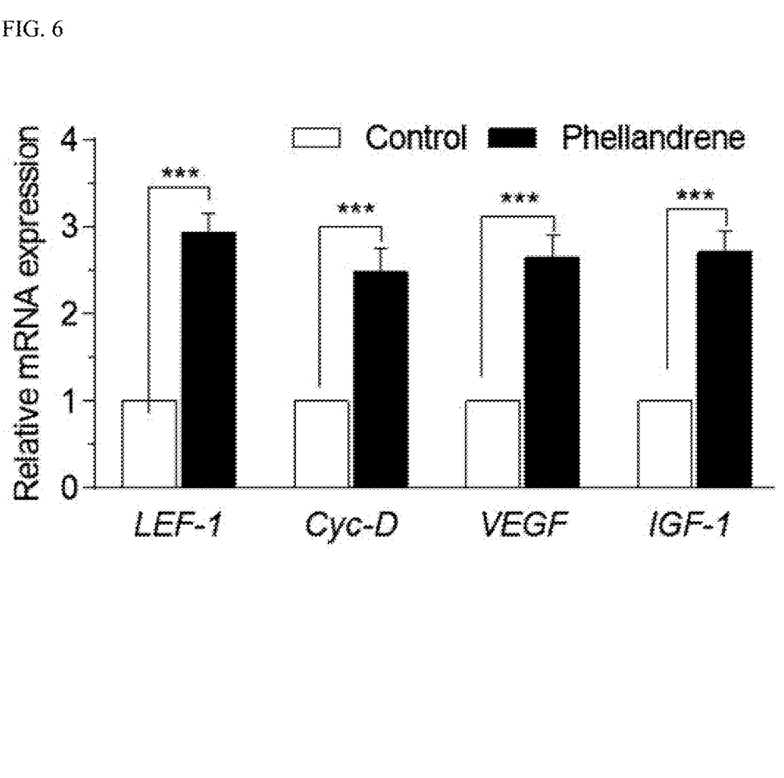
FIG. 6 illustrates a graph showing an effect of phellandrene on increase in expression of hair development promotion-related genes (LEF-1, Cyc-D, VEGF, and IGF-1) in human hair dermal papilla cells. Each value is expressed as mean±standard error (SEM). ns=p>0.05, *=p<0.05, =p<0.01, *=p<0.001 [one-way ANOVA, Tukey's test]

4) Effect of Phellandrene on Increase in Expression of Hair Development Regulation Signaling Genes (LEF-1, Cyc-D, VEGF, and IGF-1) in Human Hair Dermal Papilla Cells LEF is known as an important transcription factor that regulates expression of cyclin D (Cyc-D) by binding to β-catenin in the cell nucleus, and Cyc-D is a target gene for wnt/β-catenin signal transduction. Phellandrene significantly increased mRNA expression of LEF, a transcription factor of the wnt/β-catenin signaling system, and Cyc-D, a target gene, by 348% and 250%, respectively (FIG. 6). Therefore, it can be seen that phellandrene has an effect of activating hair development regulation signaling.

Meanwhile, VEGF and IGF-1 are growth factors that promote angiogenesis in hair follicles at their resting phase so that the hair follicles are induced to enter their growth phase and differentiation of hair follicle cells is promoted. Phellandrene significantly increased mRNA expression of VEGF and IGF by 247% and 217%, respectively (FIG. 6). Therefore, it can be seen that phellandrene has an excellent hair growth promotion effect, from the viewpoint of inducing hair follicles at their resting phase to enter their growth phase.

Hereinafter, preparation examples for drug products, foods, or cosmetics, which contain phellandrene as an active ingredient, according to the present invention, are described. However, such examples are not intended to limit the present invention, but merely to specifically describe the present invention. Drug, food, or cosmetic compositions of Preparation Examples 1 to 3 were prepared, according to conventional methods, in compliance with the following compositional ingredients and compositional ratios using the ingredients having an excellent effect of preventing and treating a hair loss condition or ameliorating hair loss.

[Preparation Example 1] Preparation of Pharmaceutical Composition

| <1-1> Preparation of powders | |
| --- | --- |
| Phellandrene | 20 mg |
| Lactose hydrate | 100 mg |
| Talc | 10 mg |

The above ingredients were mixed, and the mixture was filled in an airtight bag to prepare powders.

| <1-2> Preparation of tablets | |
| --- | --- |
| Phellandrene | 10 mg |
| Corn starch | 100 mg |
| Lactose hydrate | 100 mg |
| Magnesium stearate | 2 mg |

The above ingredients were mixed, and then tableted according to a conventional tablet preparation method, to prepare tablets.

| <1-3> Preparation of capsules | |
| --- | --- |
| Phellandrene | 10 mg |
| Microcrystalline cellulose | 3 mg |
| Lactose hydrate | 14.8 mg |
| Magnesium Stearate | 0.2 mg |

The above ingredients were mixed, and then filled in gelatin capsules according to a conventional capsule preparation method, to prepare capsules.

| <1-4> Preparation of injections | |
| --- | --- |
| Phellandrene | 10 mg |
| Mannitol | 180 mg |
| Sterile distilled water for injection | 2974 mg |
| Sodium monohydrogen phosphate | 26 mg |

The above ingredients were mixed, and then made into injections to have the above contents of ingredients per ampoule (2 ml) according to a conventional injection preparation method.

| <1-5> Preparation of liquids | |
| --- | --- |
| Phellandrene | 10 mg |
| Isomerized sugar | 10 mg |
| Mannitol | 5 mg |
| Purified water | adequate amount |
| Lemon flavor | adequate amount |

According to a conventional liquid preparation method, the above respective ingredients were added in purified water and dissolved therein. An adequate amount of the lemon flavor was added therein, and then purified water was added to adjust the total amount to 100 mL. Then, sterilization was performed and a brown bottle was filled with the resultant, to prepare liquids.

[Preparation Example 2] Preparation of Health Foods

| <2-1> Preparation of health supplement food | |
|---|---|
| Phellandrene | 10 mg |
| Vitamin mixture | adequate amount |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Mineral mixture | adequate amount |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 30 mg |
| Calcium carbonate | 100 mg |
| Magnesium chloride | 24.8 mg |

For compositional proportions of the above-mentioned vitamin and mineral mixtures, ingredients that are relatively suitable for health foods were mixed in a preferred embodiment. However, blending proportions thereof may be changed in a predetermined manner for practicing the present invention. According to a conventional health food preparation method, the above ingredients may be mixed, and then granules may be prepared therefrom. The granules may be used for preparing health food compositions according to a conventional method.

| <2-2> Preparation of health beverages | |
|---|---|
| Phellandrene | 10 mg |
| Vitamin C | 15 g |
| Vitamin E (powder) | 100 g |
| Iron lactate | 19.75 g |
| Zinc oxide | 3.5 g |
| Nicotinamide | 3.5 g |
| Vitamin A | 0.2 g |
| Vitamin B1 | 0.25 g |
| Vitamin B2 | 0.3 g |
| Purified water | adequate amount |

According to a conventional health beverage preparation method, the above ingredients were mixed and then the mixture was stirred and heated at 85° C. for about 1 hour. Then, the resulting solution was filtered and brought into a 2-L sterilized container. The container was sealed and sterilized, and refrigerated. Then, the solution was used for preparing a health beverage composition of the present invention.

For the above-mentioned compositional proportions, ingredients that are relatively suitable for favorite beverages were mixed in a preferred embodiment. However, blending proportions thereof may be changed in a predetermined manner for practicing the present invention, depending on regional or national preference such as demanding classes, demanding countries, and intended uses.

[Preparation Example 3] Preparation of Cosmetic Compositions

Hereinafter, preparation examples of cosmetic compositions containing an extract of the present invention will be described. However, such examples are not intended to limit the present invention but merely to specifically describe the present invention.

| <3-1> Nourishing lotion (milk lotion) | |
|---|---|
| Phellandrene | 2.0 wt % |
| Squalane | 5.0 wt % |
| Beeswax | 4.0 wt % |
| Polysorbate 60 | 1.5 wt % |
| Sorbitan sesquioleate | 1.5 wt % |
| Liquid paraffin | 0.5 wt % |
| Caprylic or capric triglyceride | 5.0 wt % |
| Glycerine | 3.0 wt % |
| Butylene glycol | 3.0 wt % |
| Propylene glycol | 3.0 wt % |
| Carboxyvinyl polymer | 0.1 wt % |
| Triethanolamine | 0.2 wt % |
| Preservative, pigment, and fragrance | adequate amount |
| Purified water | to 100 wt % |

For the above-mentioned compositional proportions, ingredients that are relatively suitable for nourishing lotion were mixed in a preferred embodiment. However, blending proportions thereof may be changed in a predetermined manner for practicing the present invention, and preparation may be carried out according to a conventional preparation method in the cosmetic field.

| <3-2> Softening lotion (skin lotion) | |
|---|---|
| Phellandrene | 2.0 wt % |
| Glycerin | 3.0 wt % |
| Butylene glycol | 2.0 wt % |
| Propylene glycol | 2.0 wt % |
| Carboxyvinyl polymer | 0.1 wt % |
| PEG 12 nonylphenylether | 0.2 wt % |
| Polysorbate 80 | 0.4 wt % |
| Ethanol | 10.0 wt % |
| Triethanolamine | 0.1 wt % |
| Preservative, pigment, and fragrance | adequate amount |
| Purified water | to 100 wt % |

For the above-mentioned compositional proportions, ingredients that are relatively suitable for softening lotion were mixed in a preferred embodiment. However, blending proportions thereof may be changed in a predetermined manner for practicing the present invention, and preparation may be carried out according to a conventional preparation method in the cosmetic field.

| <3-3> Nourishing cream | |
|---|---|
| Phellandrene | 2.0 wt % |
| Polysorbate 60 | 1.5 wt % |
| Sorbitan sesquioleate | 0.5 wt % |
| PEG 60 hydrogenated castor oil | 2.0 wt % |
| Liquid paraffin | 10 wt % |
| Squalane | 5.0 wt % |
| Caprylic or capric triglyceride | 5.0 wt % |
| Glycerin | 5.0 wt % |
| Butylene glycol | 3.0 wt % |

| <3-3> Nourishing cream | |
| --- | --- |
| Propylene glycol | 3.0 wt % |
| Triethanolamine | 0.2 wt % |
| Preservative | adequate amount |
| Pigment | adequate amount |
| Fragrance | adequate amount |
| Purified water | to 100 wt % |

For the above-mentioned compositional proportions, ingredients that are relatively suitable for nourishing cream were mixed in a preferred embodiment. However, blending proportions thereof may be changed in a predetermined manner for practicing the present invention, and preparation may be carried out according to a conventional preparation method in the cosmetic field.

| <3-4> Massage cream | |
| --- | --- |
| Phellandrene | 1.0 wt % |
| Beeswax | 10.0 wt % |
| Polysorbate 60 | 1.5 wt % |
| PEG 60 hydrogenated castor oil | 2.0 wt % |
| Sorbitan sesquioleate | 0.8 wt % |
| Lquid paraffin | 40.0 wt % |
| Squalane | 5.0 wt % |
| Caprylic or capric triglyceride | 4.0 wt % |
| Glycerin | 5.0 wt % |
| Butylene glycol | 3.0 wt % |
| Propylene glycol | 3.0 wt % |
| Triethanolamine | 0.2 wt % |
| Preservative, pigment, and fragrance | adequate amount |
| Purified water | to 100 wt % |

For the above-mentioned compositional proportions, ingredients that are relatively suitable for massage cream were mixed in a preferred embodiment. However, blending proportions thereof may be changed in a predetermined manner for practicing the present invention, and preparation may be carried out according to a conventional preparation method in the cosmetic field.

| <3-5> Pack | |
| --- | --- |
| Phellandrene | 1.0 wt % |
| Polyvinyl alcohol | 13.0 wt % |
| Sodium carboxymethylcellulose | 0.2 wt % |
| Glycerin | 5.0 wt % |
| Allantoin | 0.1 wt % |
| Ethanol | 6.0 wt % |
| PEG 12 nonylphenyl ether | 0.3 wt % |
| Polysorbate 60 | 0.3 wt % |
| Preservative, pigment, and fragrance | adequate amount |
| Purified water | to 100 wt % |

For the above-mentioned compositional proportions, ingredients that are relatively suitable for pack were mixed in a preferred embodiment. However, blending proportions thereof may be changed in a predetermined manner for practicing the present invention, and preparation may be carried out according to a conventional preparation method in the cosmetic field.

| <3-6> Gel | |
| --- | --- |
| Phellandrene | 0.5 wt % |
| Eethylenediamine sodium acetate | 0.05 wt % |
| Glycerin | 5.0 wt % |
| Carboxyvinyl polymer | 0.3 wt % |
| Ethanol | 5.0 wt % |
| PEG 60 hydrogenated castor oil | 0.5 wt % |
| Triethanolamine | 0.3 wt % |
| Preservative, pigment, and fragrance | adequate amount |
| Purified water | to 100 wt % |

For the above-mentioned compositional proportions, ingredients that are relatively suitable for gel were mixed in a preferred embodiment. However, blending proportions thereof may be changed in a predetermined manner for practicing the present invention, and preparation may be carried out according to a conventional preparation method in the cosmetic field.

For the above-mentioned compositional proportions, ingredients that are relatively suitable for cosmetic compositions were mixed in a preferred embodiment. However, the present invention may be applied to cosmetics for various uses including other color cosmetics, and may be used for preparing a medicament which can be applied thinly on a human body, that is, an ointment, depending on efficacy thereof. Blending proportions thereof may be changed in a predetermined manner for practicing the present invention, depending on regional or national preference such as demanding classes, demanding countries, and intended uses.

The foregoing description of the present invention is provided for illustration. It will be understood by those skilled in the art that various changes and modifications can be easily made without departing from the technical spirit or essential features of the present invention. Therefore, it is to be understood that the above-described examples are illustrative in all aspects and not restrictive.

The invention claimed is:

1. A method for preventing or treating hair loss, or promoting hair development or hair growth, the method comprising administering a composition including α-phellandrene or β-phellandrene or a pharmaceutically acceptable salt thereof as an active ingredient, applying the composition or allowing the composition to be taken.

2. The method according to claim 1, wherein the composition increases expression of at least one selected from the group consisting of β-catenin, protein kinase A Cα (PKA Cα), lymphoid enhancer factor-1 (LEF-1), insulin-like growth factor-1 (IGF-1), vascular endothelial growth factor (VEGF), and cyclin D.

3. The method according to claim 1, wherein the composition is a pharmaceutical composition, a quasi-drug composition, a cosmetic composition or a health functional food composition.

4. The method according to claim 3, wherein the pharmaceutical composition is a formulation for skin external use which is selected from the group consisting of a cream, a gel, a patch, a spray, an ointment, a plaster, a lotion, a liniment, a paste, and a cataplasm.

5. The method according to claim 3, wherein the cosmetic composition is a formulation which is a scalp tonic, a scalp lotion, a scalp cream, a scalp serum, a scalp essence, a scalp ampoule, a scalp treatment, a scalp conditioner, a scalp shampoo, a scalp pack, a hair tonic, a hair lotion, a hair cream, a hair spray, a hair mousse, a hair gel, a hair conditioner, a hair shampoo, a hair conditioning rinse, a hair pack, a hair treatment, an eyebrow growth solution, an eyelash growth solution, an eyelash enhancer, a shampoo for pets, or a conditioner for pets.

* * * * *